United States Patent [19]

Bick

[11] Patent Number: 4,940,731

[45] Date of Patent: Jul. 10, 1990

[54] METHOD OF TREATING PREMATURE EJACULATION USING SERTRALINE

[75] Inventor: Peter A. Bick, Hartsdale, N.Y.

[73] Assignee: Pfizer Inc., New York, N.Y.

[21] Appl. No.: 400,417

[22] Filed: Aug. 30, 1989

[51] Int. Cl.$^5$ .............................................. A61K 31/135
[52] U.S. Cl. ................................................... 514/657
[58] Field of Search ......................................... 514/657

[56] References Cited

U.S. PATENT DOCUMENTS 4,029,731  6/1977  Sarges .................................. 514/657
4,536,518  8/1985  Welch, Jr. et al. .................. 514/647

Primary Examiner—Leonard Schenkman
Attorney, Agent, or Firm—Peter C. Richardson; Paul H. Ginsburg; Karen DeBenedictis

[57] ABSTRACT

A method of treating premature ejaculation comprising administering to a human in need of such treatment an amount of the compound (1S-cis)-4-(3,4-dichlorophenyl)-1,2,3,4-tetrahydro-N-methyl-1-naphthalenamine, also known by the generic name sertraline, or a pharmaceutically acceptable salt thereof, effective in delaying ejaculation.

1 Claim, No Drawings

METHOD OF TREATING PREMATURE EJACULATION USING SERTRALINE

This invention relates to a method of treating premature ejaculation using the compound (1S-cis)-4-(3,4-dichlorophenyl)-1,2,3,4-tetrahydro-N-methyl-1-naphthalenamine, hereinafter referred to by its generic name "sertraline", or a pharmaceutically acceptable salt thereof.

Sertraline, which has the empiral formula $C_{12}H_{17}NCl_2$ and the structural formula

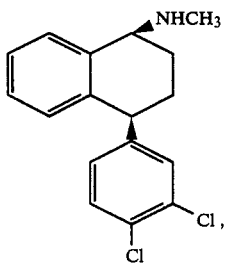

is a known antidepressant and anorectic agent. U.S. Pat. No. 4,536,518, assigned in common with the present invention and hereby incorporated herein by reference, discloses sertraline and related compounds of the formula

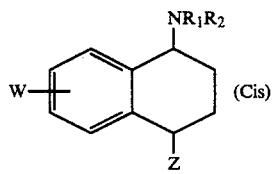

wherein Z is

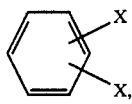

and $R_1$, $R_2$, W, X and Y are as defined therein, and states that such compounds exhibit antidepressant and anorectic activity in vivo in mammals.

The present invention relates to a method of treating premature ejaculation, comprising administering to a patient in need of such treatment an amount of sertraline, or a pharmaceutically acceptable salt thereof, effective in delaying ejaculation.

Examples of pharmaceutically acceptable salts of sertraline that can be used to treat premature ejaculation in accordance with the present invention are the acid addition salts of various mineral and organic acids such as hydrochloric, hydrobromic, hydroiodide, sulfuric, phosphoric, acetic, lactic, maleic, fumaric, citric, tartaric, succinic, and gluconic.

Sertraline may be used to delay ejaculation in patients treated with the drug. This effect does not persist after treatment with the drug is discontinued. Other compounds of the formula I above may be similarly effective.

Sertraline may be prepared as described in U.S. Pat. No. 4,536,518, and particularly, in Example 2 of that patent.

Sertraline, or a pharmaceutically acceptable salt thereof, when used to treat a premature ejaculation, may be administered either orally or parenterally. It is generally administered in dosages ranging from about 50-200 mg per day, although variations will necessarily occur depending upon the condition of the subject being treated and the particular route of administration chosen. It may be administered either alone or in combination with pharmaceutically acceptable carriers by either of the above routes, and such administration can be carried out in both single and multiple dosages. More particularly, sertraline, or a pharmaceutically acceptable salt thereof, may be administered in a wide variety of different dosage forms, i.e., it may be combined with various pharmaceutically acceptable inert carriers in the form of tablets, capsules, lozenges, troches, hand candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, sertraline, or a pharmaceutically acceptable salt thereof, when used to treat a chemical dependency, is present in such dosage forms at concentration levels ranging from about 0.5% to about 90% by weight of the total composition, i.e., in amounts that are sufficient to provide the desired unit dosage. It may exist in different polymorphic forms, i.e. different crystalline forms.

For purposes of oral administration, tablets containing various excipients such as sodium citrate, calcium carbonate and calcium phosphate may be employed along with various disintegrants such as starch, preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred fillers would also include lactose or milk sugar as well as high molecular weight polyethylene glycols. When aqueous suspensions and/or elixers are desired for oral administration, the sertraline, or pharmaceutically acceptable salt thereof, may be combined with various sweetening or flavoring agents, coloring matter or dyes and, if so desired, emulsifying and/or suspending agents, together with diluents such as water, ethanol, propylene glycol, glycerin and various like combinations thereof.

For purposes of parenteral administration, solutions of sertraline, or a pharmaceutically acceptable salt thereof, in sesame or peanut oil or in aqueous propylene glycol or N,N-dimethylformamide may be employed, as well as sterile aqueous solutions of the water-soluble, non-toxic mineral and organic acid addition salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

A typical dry solid pharmaceutical composition is prepared by blending the following materials together in the proportions by weight specified below:

Cis-(1S)-N-methyl-4-(3,4-dichlorophenyl)-1, 2,3,4-tetrahydro-1-naphthalenamine hydrochloride: 50
  Sodium citrate: 25
  Alginic acid: 10
  Polyvinylpyrrolidone: 10
  Magnesium stearate: 5

After the dried composition is thoroughly blended, tablets are punched from the resulting mixture, each tablet being of such size that it contains 100 mg of sertraline hydrochloride. Other tablets are also prepared in a similar fashion containing 5, 10, 25, and 50 mg of sertraline hydrochloride respectively, by using the appropriate amount of the naphthalenamine salt in each case.

Another typical dry solid pharmaceutical composition is prepared by combining the following materials together in the proportions by weight indicated below:

Cis-(1S)-N-methyl-4-(3,4-dichlorophenyl)-1, 2,3,4-tetrahydro-1-naphthalenamine hydrochloride: 50
  Calcium carbonate: 20
  Polyethylene glycol, average molecular weight, 4000: 30

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 50 mg of the active ingredient.

What is claimed:

1. A method of treating premature ejaculation, comprising administering to a patient in need of such treatment an amount of the compound (1S-cis)-4-(3,4-dichlorophenyl)-1,2,3,4-tetrahydro-N-methyl-1-naphthalenamine, or a pharmaceutically acceptable salt thereof, effective in delaying ejaculation.

* * * * *